(12) United States Patent  
DeHoogh et al.

(10) Patent No.: US 6,659,998 B2
(45) Date of Patent: Dec. 9, 2003

(54) MAPPABLE FOOT CONTROLLER FOR MICROSURGICAL SYSTEM

(75) Inventors: Greg L. DeHoogh, Laguna Hills, CA (US); Paul J. Essex, Rancho Santa Margarita, CA (US); Donn D. Lobdell, Corona Del Mar, CA (US); Roger Thomas, Tustin, CA (US); Kirk W. Todd, Yorba Linda, CA (US)

(73) Assignee: Alcon Universal Ltd., Hunenberg (CH)

( * ) Notice: Subject to any disclaimer, the term of this patent is extended or adjusted under 35 U.S.C. 154(b) by 49 days.

(21) Appl. No.: 09/948,224

(22) Filed: Sep. 6, 2001

(65) Prior Publication Data

US 2002/0045887 A1 Apr. 18, 2002

Related U.S. Application Data

(60) Provisional application No. 60/241,059, filed on Oct. 17, 2000.

(51) Int. Cl.[7] .............................................. A61B 17/00
(52) U.S. Cl. ................................. 606/1; 606/4; 600/126
(58) Field of Search ........................ 606/1, 4; 600/126; 307/119

(56) References Cited

U.S. PATENT DOCUMENTS

| 4,837,857 | A |   | 6/1989  | Scheller et al. ............ 455/617 |
| 4,983,901 | A |   | 1/1991  | Lehmer ...................... 318/685 |
| 5,091,056 | A |   | 2/1992  | Autio ...................... 162/306.1 |
| 5,157,603 | A | * | 10/1992 | Scheller et al. ................ 606/4 |
| 5,268,624 | A |   | 12/1993 | Zanger ....................... 318/551 |
| 5,455,766 | A |   | 10/1995 | Scheller et al. |
| 5,554,894 | A | * | 9/1996  | Sepielli ...................... 307/119 |
| 5,580,347 | A |   | 12/1996 | Reimels ....................... 604/30 |
| 5,788,688 | A | * | 8/1998  | Bauer et al. ................... 606/1 |
| 5,983,749 | A |   | 11/1999 | Holtorf ........................ 74/560 |
| 6,106,512 | A | * | 8/2000  | Cochran et al. ............... 606/1 |
| 6,179,829 | B1 | * | 1/2001  | Bisch et al. ................... 606/1 |

FOREIGN PATENT DOCUMENTS

| WO | WO 96/13845 | 5/1996 |
| WO | WO 98/08442 | 3/1998 |
| WO | WO 99/14648 | 3/1999 |
| WO | WO 00/12037 | 3/2000 |

* cited by examiner

*Primary Examiner*—Michael Peffley
*Assistant Examiner*—Jocelyn Ram
(74) *Attorney, Agent, or Firm*—W. David Lee

(57) ABSTRACT

A microsurgical system, and a method of mapping the surgical functions of the microsurgical system to a foot controller operatively coupled with the system, are disclosed. The microsurgical system includes a computer, a foot controller operatively coupled to the computer, and a touch screen display operatively coupled to the computer. The foot controller has a plurality of switches. Each of the switches is for controlling a surgical function of the microsurgical system and for actuation by a user's foot. The touch screen display has the ability to display a graphic representation of the foot controller including the plurality of switches, and to display a list of surgical functions so that the list is associated with the graphical representation of one of the plurality of switches. By touching one of the surgical functions in the list, a user can exchange the surgical functions associated with any two of the plurality of switches on the foot controller.

7 Claims, 10 Drawing Sheets

MAPPABLE FOOT CONTROLLER FOR MICROSURGICAL SYSTEM

This application claims the benefit of U.S. Provisional Application No. 60/241,059, filed Oct. 17, 2000, and entitled "Mappable Foot Controller for Microsurgical System".

FIELD OF THE INVENTION

The present invention generally pertains to microsurgical systems. More particularly, but not by way of limitation, the present invention pertains to foot controllers for the operation of such systems, as well as the customization of such foot controllers for particular surgeons and surgical procedures.

DESCRIPTION OF THE RELATED ART

Various foot controllers are used to control microsurgical systems, and particularly ophthalmic microsurgical systems. During ophthalmic surgery, a surgeon views the patient's eye through an operating microscope. To control the microsurgical system and its associated handpieces during the various portions of the surgical procedure, the surgeon must either instruct a nurse how to alter the machine settings on the surgical system, or use the foot controller to change such settings. Where possible, many surgeons prefer to use the foot controller to alter the machine settings on the surgical system, eliminating the need to converse with a nurse during the surgical procedure.

Many conventional foot controllers have a foot pedal that provides linear control of the functions of the surgical system or an associated handpiece, and a series of switches or buttons that provide binary control of such functions. Exemplary foot controllers for ophthalmic microsurgical systems are disclosed in International Publication Number WO 00/12037; International Publication Number WO 99/14648; International Publication Number WO 98/08442; International Publication No. WO 96/13845; U.S. Pat. No. 5,983,749; U.S. Pat. No. 5,580,347; U.S. Pat. No. 4,837,857; U.S. Pat. No. 4,983,901; U.S. Pat. No. 5,091,056; U.S. Pat. No. 5,268,624; U.S. Pat. No. 5,554,894, all of which are incorporated herein by reference.

International Publication Number WO 98/08442 discloses a foot controller for a microsurgical system that allows a surgeon to program certain aspects of the controller. However, many surgeons desire the ability to truly customize foot controllers for microsurgical systems. The present invention is directed to a microsurgical system and foot controller that provide such flexibility.

SUMMARY OF THE INVENTION

The microsurgical system of the present invention includes a computer, a foot controller operatively coupled to the computer, and a touch screen display operatively coupled to the computer. The foot controller has a plurality of switches. Each of the switches is for controlling a surgical function of the micro surgical system and for actuation by a user's foot. The touch screen display has the ability to display a graphic representation of the foot controller including the plurality of switches, and to display a list of surgical functions so that the list is associated with the graphical representation of one of the plurality of switches. By touching one of the surgical functions in the list, a user can exchange the surgical functions associated with any two of the plurality of switches on the foot controller.

BRIEF DESCRIPTION OF THE DRAWINGS

For a more complete understanding of the present invention, and for further objects and advantages thereof, reference is made to the following description taken in conjunction with the accompanying drawings in which.

DETAILED DESCRIPTION OF THE PREFERRED EMBODIMENTS

The preferred embodiments of the present invention and their advantages are best understood by referring to FIGS. 1 through 11 of the drawings, like numerals being used for like and corresponding parts of the various drawings.

Figure 1:
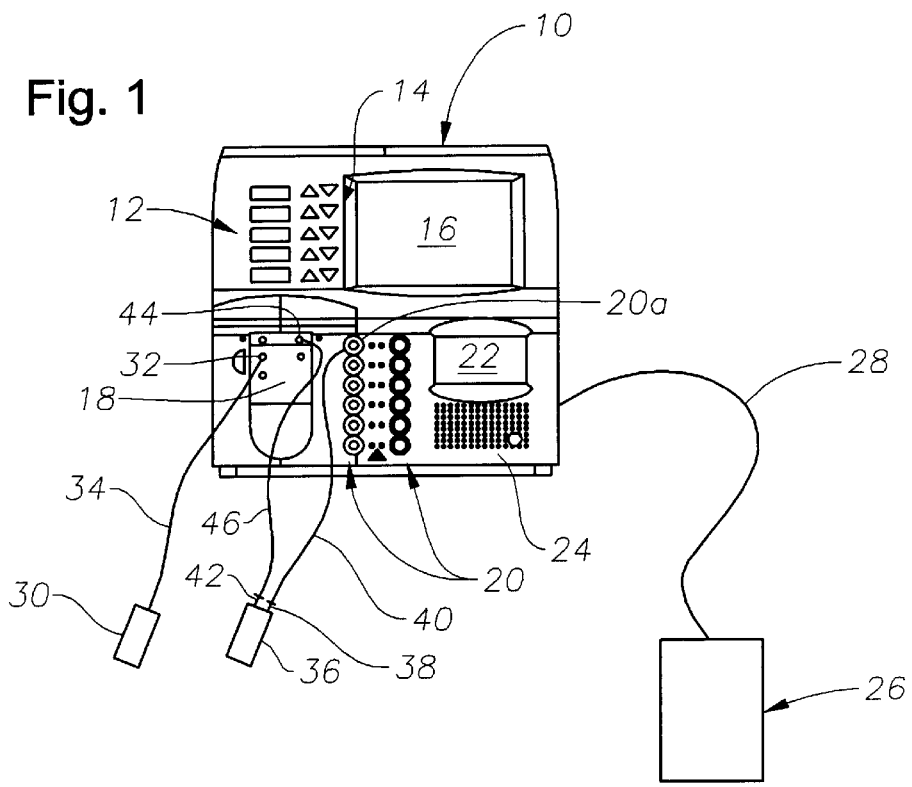
FIG. 1 is a front, schematic view of a microsurgical system according to a preferred embodiment of the present invention.

FIG. 1 shows a microsurgical system 10 according to a preferred embodiment of the present invention. As shown in FIG. 1, microsurgical system 10 is an ophthalmic microsurgical system. However, microsurgical system 10 may be any microsurgical system, including a system for performing otic, nasal, throat, or other surgeries.

System 10 preferably includes a series of light emitting diode ("LED") displays 12 for displaying system parameters, a series of "up/down" arrows keys 14 for altering the system parameters displayed on LED displays 12, a liquid crystal display ("LCD") 16 with touch screen capability, a surgical cassette 18, a series of electrical and pneumatic connectors or ports 20 for operatively coupling with the various surgical handpieces associated with system 10, an illuminator module 22, and a speaker 24. A foot controller 26 is operatively coupled to system 10 via conventional electronic cable 28. As mentioned above, a series of handpieces are operatively coupled to system 10 during ophthalmic surgery. Exemplary handpieces utilized in anterior segment ophthalmic surgery include an irrigation handpiece, an irrigation/aspiration handpiece, an ultrasonic handpiece, and/or a diathermy handpiece. A preferred ultrasonic handpiece is a phacoemulsification handpiece. Exemplary handpieces utilized in posterior segment ophthalmic surgery include an extrusion handpiece, an infusion cannula, a victrectomy probe, microsurgical scissors, and/or a diathermy handpiece. By way of example, in FIG. 1 an infusion cannula 30 is shown fluidly coupled to an irrigation outlet 32 of surgical cassette 18 via conventional medical grade flexible tubing 34. Also by way of example, a vitrectomy probe 36 is shown in FIG. 1. Pneumatic drive port 38 of probe 36 is fluidly coupled to pneumatic pressure port 20a of system 10 via conventional medical grade flexible tubing 40. Aspiration port 42 of probe 36 is fluidly coupled to an aspiration port 44 of cassette 18 via conventional medical grade flexible tubing 46.

Figure 2:
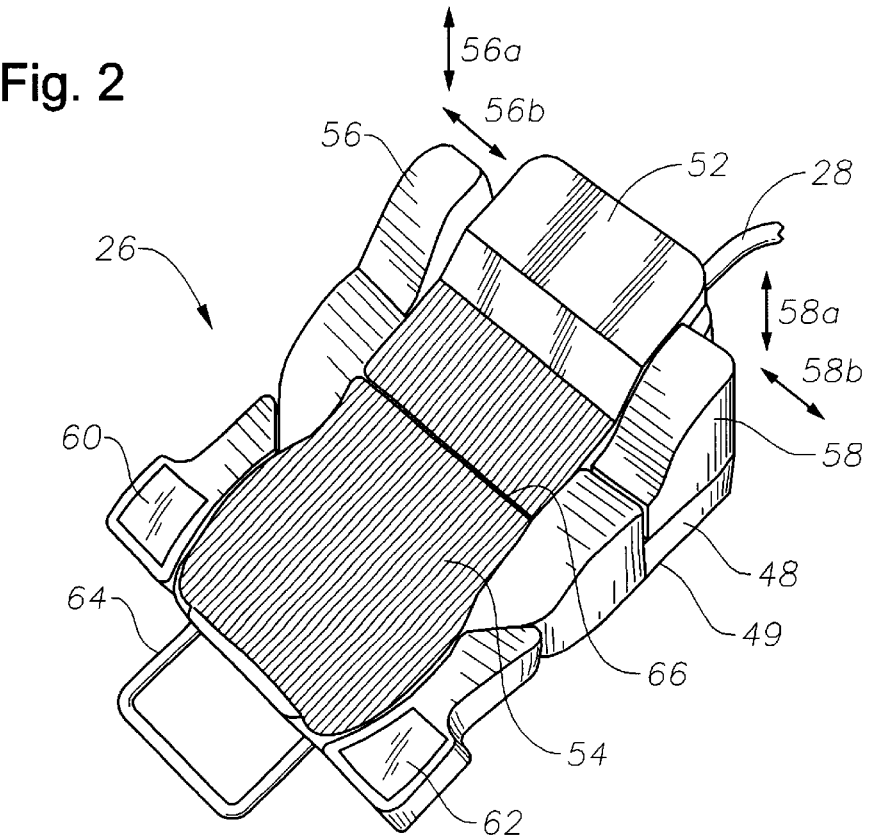
FIG. 2 is perspective view of a preferred embodiment of a foot controller for the microsurgical system of FIG. 1.

FIG. 2 shows a front, perspective view of a preferred embodiment of foot controller 26. Foot controller 26 has a body 48 with a base 49 that supports foot controller 26 on the operating room floor. Body 48 preferably includes a foot pedal 52, a heel rest 54, a left toe switch 56, a right toe switch 58, a left heel switch 60, a right heel switch 62, and a handle 64.

Foot pedal 52 is rotationally coupled to body 48 along line 66. Foot pedal 52 may be depressed using the upper portion of a surgeon's foot to move from a fully undepressed position, as shown in FIG. 2, to a fully depressed position in which foot pedal 52 lies in generally the same plane as heel rest 54. Foot pedal 52 is used by the surgeon to provide linear control to certain functions of microsurgical system 10. By way of example, depending on the operating mode of system 10, foot pedal 10 may be used to provide proportional control of vitrectomy probe cut rate, ultrasonic handpiece power, or vacuum level delivered to a handpiece.

Left toe switch 56 is a dual mode binary switch. The first mode of switch 56 is actuated when a surgeon presses downward on switch 56 with his or her toe. This first mode is referred to herein as left vertical switch 56a. The second mode of switch 56 is actuated when a surgeon presses in a generally outward, horizontal direction on switch 56 with the side of his or her foot. This second mode is referred to herein as left horizontal switch 56b. Switch 56 is preferably a momentary actuation type switch that provides tactile feedback to the user. Switch 56 is preferably constructed using two Part Number P3-30125 switches available from Otto Controls of Carpenterville, Ill., one for left vertical switch 56a, and a second for left horizontal switch 56b.

Right toe switch 58 is also a dual mode binary switch. The first mode of switch 58 is actuated when a surgeon presses downward on switch 58 with his or her toe. This first mode is referred to herein as right vertical switch 58a. The second mode of switch 58 is actuated when a surgeon presses in a generally outward, horizontal direction on switch 58 with the side of his or her foot. This second mode is referred to herein as right horizontal switch 58b. Switch 58 is preferably a momentary actuation type switch that provides tactile feedback to the user, and is preferably constructed in the same manner as switch 56.

Left heel switch 60 is a binary switch that is actuated when a surgeon presses downward with his or her heel. Right heel switch 62 is a binary switch that is actuated when a surgeon presses downward with his or her heel. Switches 60 and 62 are preferably momentary actuation type switches that provide tactile feedback to the user. Switches 60 and 62 are each preferably constructed using a Part Number P3-30125 switch available from Otto Controls of Carpenterville, Ill.

Foot controller 26 may be made using conventional technology. Foot controller 26 is preferably similar in construction to the foot controller sold with the Accurus® surgical system available from Alcon Laboratories, Inc. of Fort Worth, Tex., except that controller 26 has been modified to include an additional binary switch, right heel switch 60.

Figure 3:
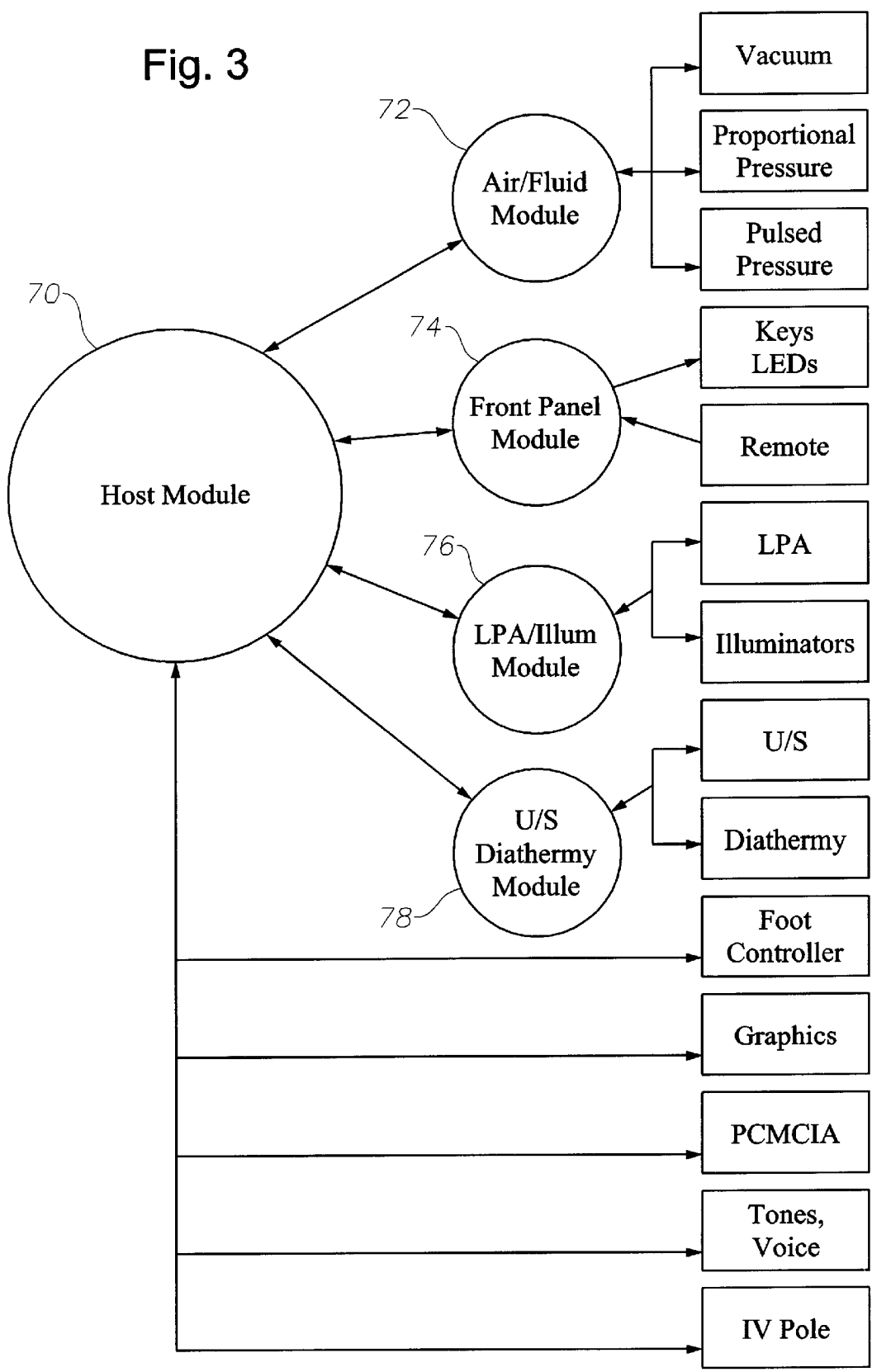
FIG. 3 is a block diagram of the preferred hardware and software configuration for the microsurgical system of FIG. 1.

FIG. 3 is a high-level block diagram of the preferred hardware and software configuration of microsurgical system 10. System 10 preferably includes a Host module 70, an Air/Fluid module 72, a Front Panel module 74, a Low Pressure Air ("LPA")/Illumination module 76, and an Ultrasound ("U/S")/Diathermy module 78. Host module 70 is preferably personal computer based, and modules 72, 74, 76, and 78 are each preferably a microcontroller. Host module 70 and modules 72 through 78 preferably communicate with each other over dedicated serial lines. The hardware configuration of system 10 is preferably a star topology.

Host module 70 software communicates with each of modules 72 through 78 to maintain system 10 status, to direct system 10 functionality, and to mitigate hazard conditions. Host module 70 software also monitors and controls foot controller 26, including each of the binary switches of controller 26; displays graphics and data on display 16; monitors and controls PCMCIA card access; generates audio tones and voices for speaker 24; and controls the motorized IV pole (not shown) of system 10. The PCMCIA card is used to upload and download software into system 10.

Air/Fluid module 72 software controls the vacuum source, proportional pressure source, and pulsed pressure source of system 10. Front panel module 74 software creates screens for display 16, scans for presses of keys 14 or the buttons or arrows on the touch screen of display 16, receives remote control input, and outputs LED displays 12. Screens for display 16 are created using a conventional software such as Zinc available from Wind River of Alameda, Calif. The LPA/Illumination module 76 software controls the low pressure air source of system 10 and the illuminators stored in illuminator module 22. U/S/Diathermy module 78 software controls ultrasonic power and diathermy handpiece voltage.

Figure 4:
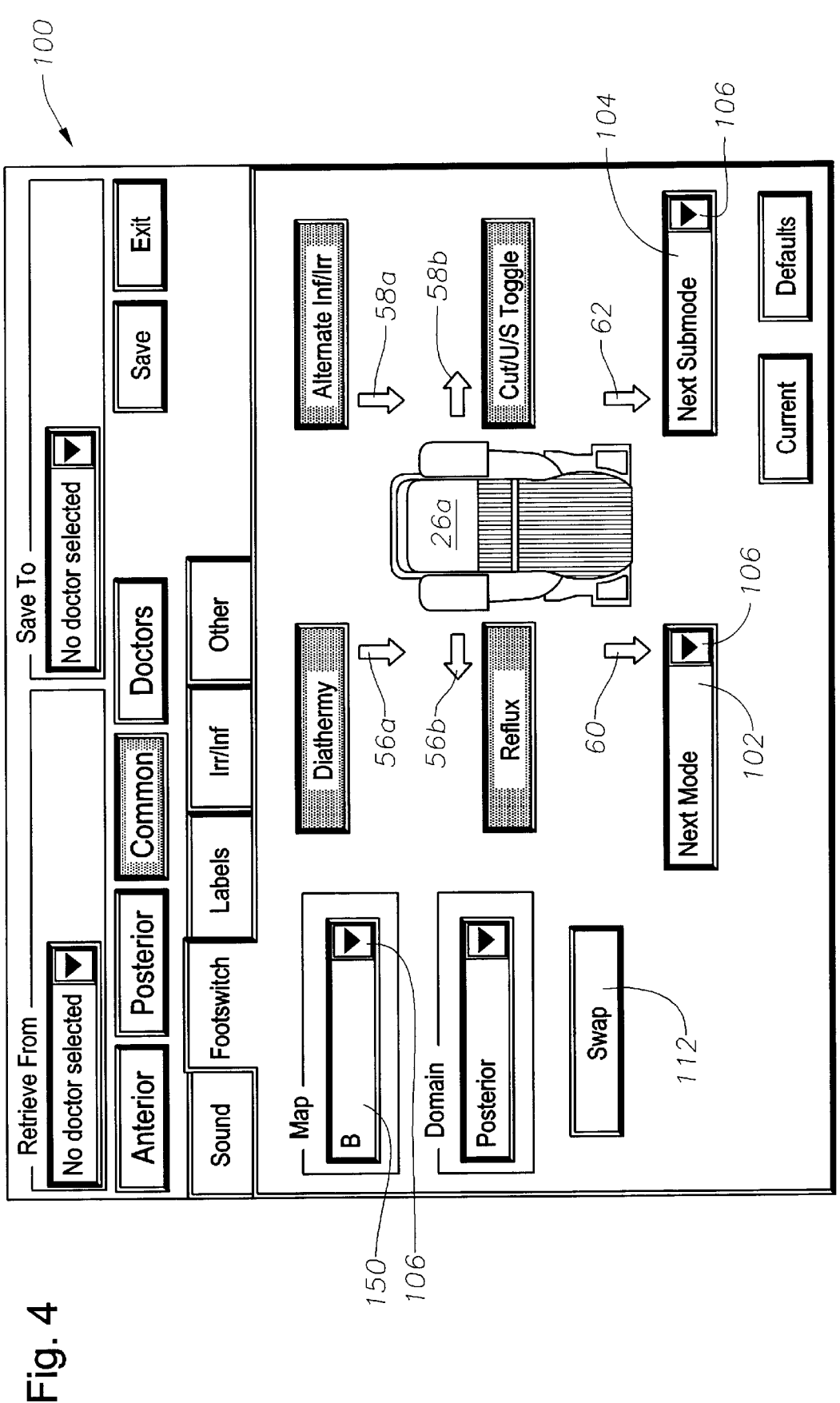
FIG. 4 is a touch screen display of the microsurgical system of FIG. 1 showing a first preferred embodiment of a screen utilized to set up the foot controller of FIG. 2.

FIG. 4 shows a first preferred embodiment of a screen 100 utilized to set up foot controller 26. Preferably, system 10 only allows one specific set up of foot controller 26 for each surgeon or doctor. Screen 100 is displayed on display 16. Screen 100 preferably includes a graphical representation 26a of foot controller 26, including left vertical switch 56a, left horizontal switch 56b, right vertical switch 58a, right horizontal switch 58b, left heel switch 60, and right heel switch 62. FIG. 4 shows a preferred Map B of the surgical functions of microsurgical system 10 to the switches of foot controller 26. In Map B, switch 56a is assigned the Diathermy function, switch 56b is assigned the Reflux function, switch 58a is assigned the Alternate Infusion/Irrigation function, and switch 58b is assigned the Cut/Ultrasonic Toggle function. A software generated list 102 is associated with left heel switch 60, and a software generated list 104 is associated with right heel switch 62. Left heel switch 60 is assigned a default function of Next Mode, and right heel switch 62 is assigned a default function of Next Submode.

Figure 5:
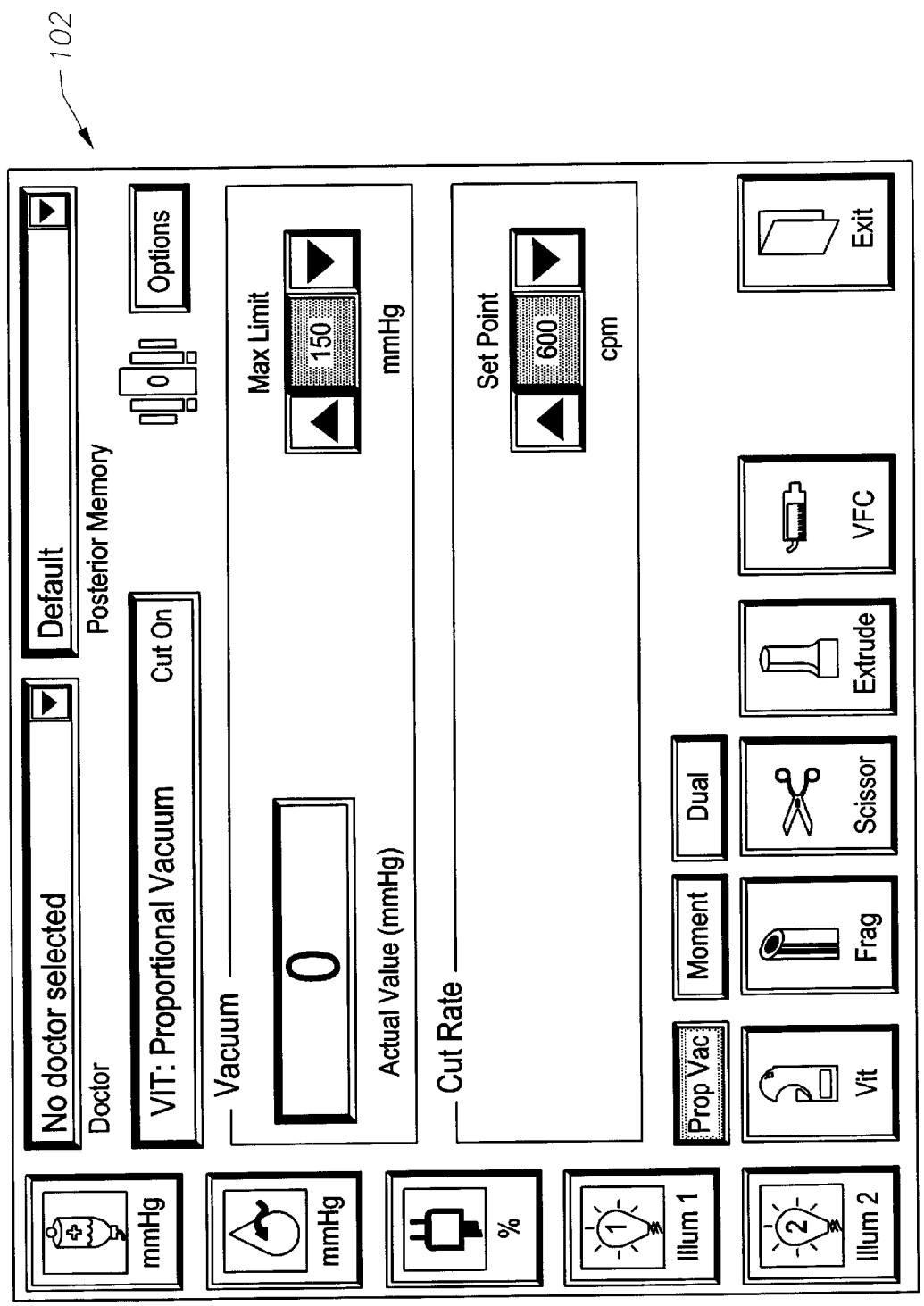
FIG. 5 is a touch screen display of the microsurgical system of FIG. 1 showing the preferred embodiment of a posterior segment domain screen.

FIG. 5 shows the preferred embodiment of a posterior segment domain screen 102 of display 16. As shown by the touch screen icons on the bottom of screen 102, exemplary posterior segment surgical modes of system 10 are vitrectomy, fragmentation, scissors, extrusion, and viscous fluid control ("VFC"). Exemplary vitrectomy submodes of system 10 are proportional vacuum, momentary, and dual proportional. When system 10 is operating in the posterior segment domain, left heel switch 60 is assigned the function of Next Mode, and a surgeon depresses and releases left heel switch 60 of foot controller 26, the surgical mode of system 10 changes from vitrectomy to fragmentation. Successive depressions of switch 60 result in mode changes from fragmentation to scissors, scissors to extrusion, extrusion to viscous fluid control, and viscous fluid control to vitrectomy. When system 10 is operating in the posterior segment domain and the vitrectomy mode, right heel switch 62 is assigned the function of Next Submode, and a surgeon depresses and releases right heel switch 62 of foot controller 26, the surgical submode of system 10 changes from proportional vacuum to momentary. Successive depressions of switch 62 result in submode changes from momentary to dual proportional, and dual proportional to proportional vacuum.

Although not shown on FIG. 5, the fragmentation, scissors, extrusion, and viscous fluid control preferably also have associated submodes. For example, fragmentation mode may include proportional, momentary, and fixed submodes; scissors mode may include proportional, multi-cut, and membrane peeler cutter submodes; extrusion mode may include low, medium, and high submodes; and viscous fluid control mode may include injection and extraction submodes. The Next Mode function and the Next Submode function work in a similar manner with these surgical modes and associated submodes.

Although not shown in FIG. 5, display 16 also preferably includes an anterior segment domain screen showing anterior segment surgical modes and submodes. By way of example, system 10 may include phacoemulsification, irrigation/aspiration, and vitrectomy anterior segment surgical modes. Each anterior segment surgical mode of system 10 preferably includes various submodes. For example, phacoemulsification mode may include linear, burst, and fixed submodes; irrigation/aspiration mode may include capsule vacuum and maximum submodes; and vitrectomy mode may include wet and dry submodes. The Next Mode function and the Next Submode function work with these anterior segment modes and associated submodes in a manner similar to that described above in connection with the posterior segment surgical modes and associated submodes.

Figure 6:
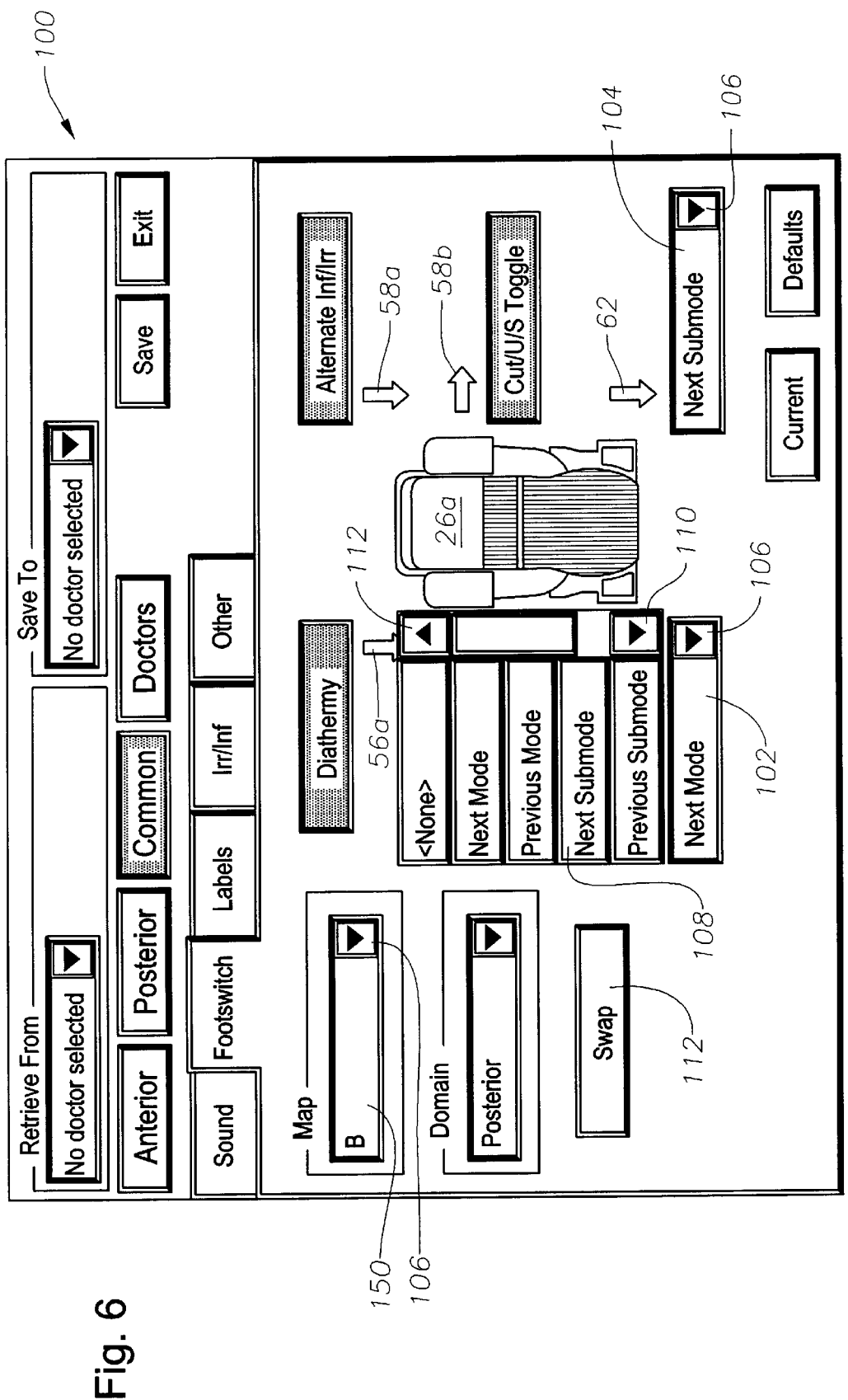
FIG. 6 is a touch screen display of the microsurgical system of FIG. 1 showing the preferred embodiment of software generated list used to select the function of a first binary switch on the foot controller of FIG. 2.

Referring again to FIG. 4, if a user touches pull down menu arrow 106 of software generated list 102 associated with left heel switch 60, a list 108 of functions appears, as shown in FIG. 6. List 108 of functions preferably includes None, Next Mode, Previous Mode, Next Submode, Previous Submode, Next Memory (not shown), and Previous Memory (not shown). The various functions of list 108 can be accessed via a user touching scroll down arrow 110 or scroll up arrow 112, as is conventional. A user can assign any function in list 108 to left heel switch 60 of controller 26 by simply touching the desired function on the touch screen of display 16. The None function renders left heel switch 60 inactive. If a user touches pull down menu arrow 106 of software generated list 104 associated with right heel switch 62, a similar list of functions appears. A user can select a desired function for right heel switch 62 in the same manner as that described above for left heel switch 60.

The Previous Mode and Previous Submode functions work in exactly the opposite manner of the Next Mode and Next Submode functions described hereinabove. By way of example, and referring to FIG. 5, when system 10 is operating in the posterior segment domain, left heel switch 60 is assigned the function of Previous Mode, and a surgeon depresses and releases left heel switch 60 of foot controller 26, the surgical mode of system 10 changes from vitrectomy to viscous fluid control. Successive depressions of switch 60 result in mode changes from viscous fluid control to extrusion, extrusion to scissors, scissors to fragmentation, and fragmentation to vitrectomy.

The Next Memory and Previous Memory functions refer to various "doctor memories" that system 10 preferably allows to be assigned to each surgeon. For example, in the anterior segment domain and phacoemulsification mode, each of submodes linear, burst, and fixed have certain operating parameters for system 10 and its associated hand pieces. The linear submode may have vacuum level, ultrasound power, pulse rate, and pulse enabled parameters. The burst mode may have vacuum level, ultrasound power, and length parameters. The fixed submode may have vacuum level, ultrasound power, pulse rate, and pulse enabled parameters. System 10 preferably allows a surgeon to create and store multiple doctor memories for the anterior segment domain, and multiple doctor memories for the posterior segment domain. These doctor memories are preferably created using the touch screen of display 16. Referring to FIG. 6, when left heel switch 60 is assigned the Next Memory function, the surgeon may cycle through the various doctor memories for the domain he or she is currently operating in by repeated depression and release of switch 60. Similarly, when right heel switch 62 is assigned the Previous Memory function, the surgeon may cycle through the various doctor memories for the domain he or she is currently operating in by repeated depression and release of switch 62. The direction of cycling of Next Memory is opposite to the direction of cycling of Previous Memory.

Figure 7:
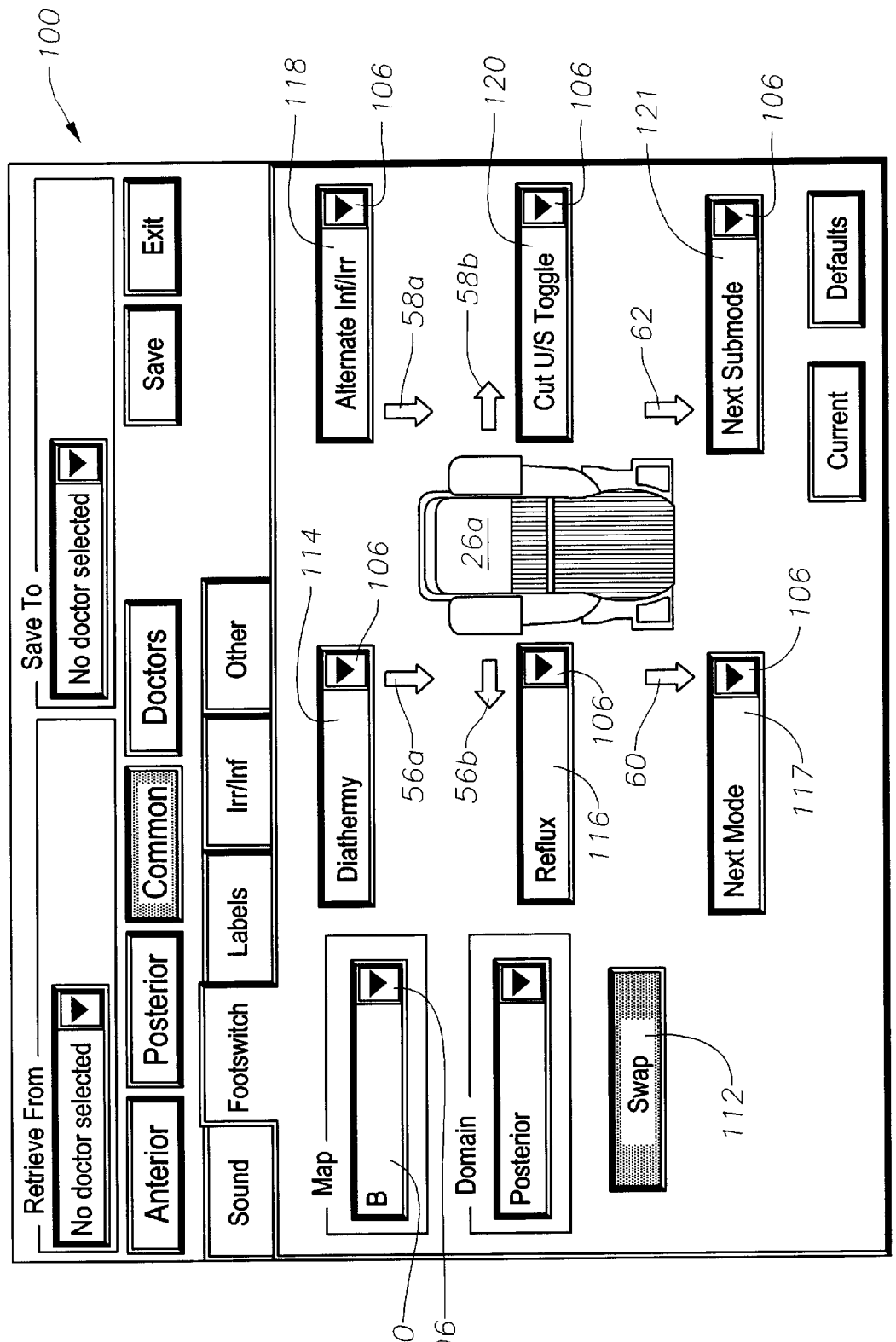
FIGS. 7–10 each show screens of the touch screen display of the microsurgical system of FIG. 1 showing the preferred method of mapping the binary switches of the foot controller of FIG. 2.
Figure 8:
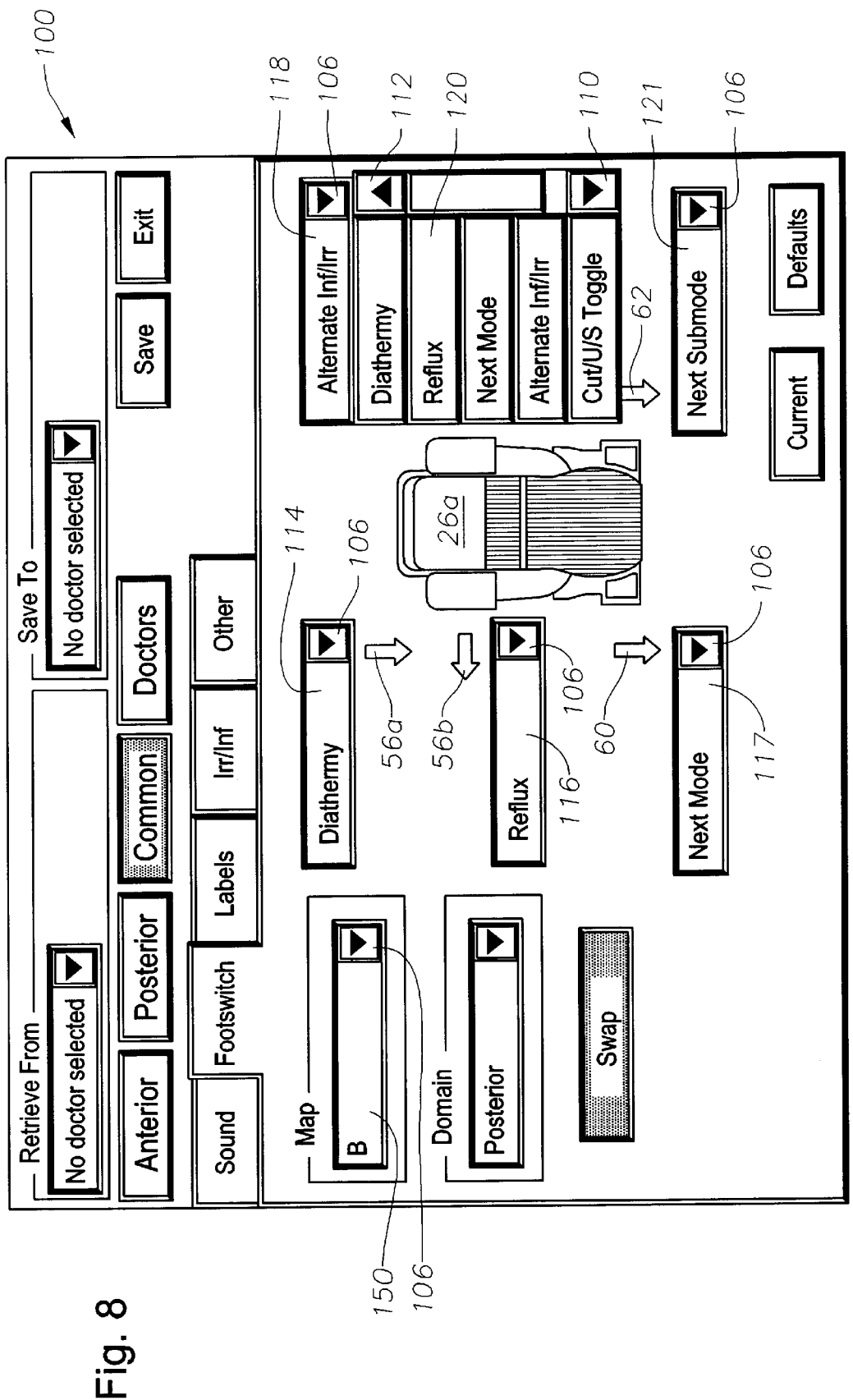
Figure 9:
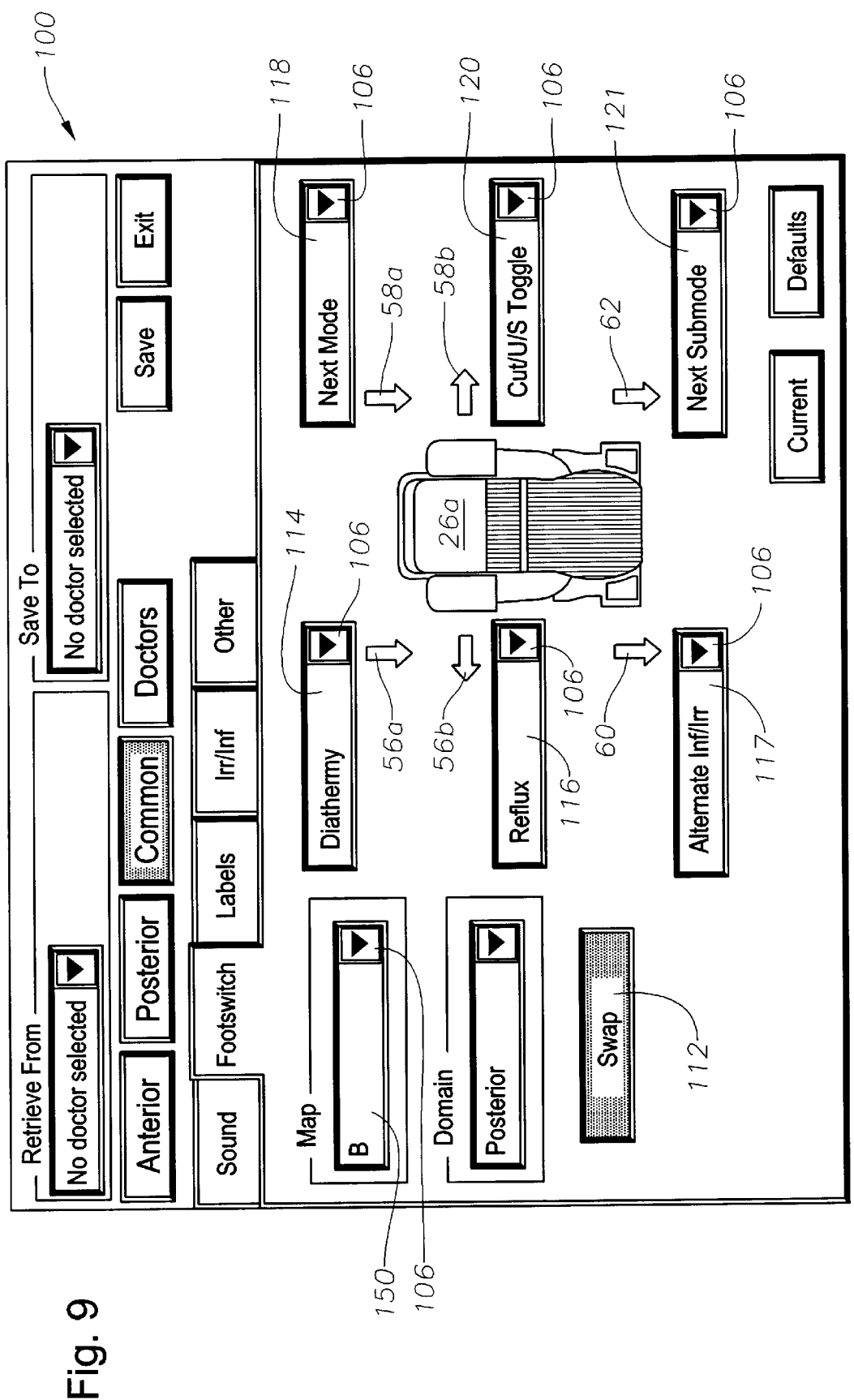

FIGS. 7–10 show screen 100 of display 16 of system 10 being used to map switches 56a, 56b, 58a, 58b, 60, and 62 of foot controller 26 according to a preferred method of the present invention. Referring to FIG. 7, screen 100 is shown after the user has depressed Swap button 112 on the touch screen. Upon depressing Swap button 112, front panel module 74 creates a software generated list 114 associated with left vertical switch 56a, a software generated list 116 associated with left horizontal switch 56b, a software generated list 117 associated with left heel switch 60, a software generated list 118 associated with right vertical switch 58a, a software generated list 120 associated with right horizontal switch 58b, and a software generated list 121 associated with right heel switch 62. Each of software generated lists 114, 116, 117, 118, 120, and 121 have a pull down menu arrow 106. As shown in FIG. 8, if a user presses pull down menu arrow 106 associated with software generated list 118, a list 120 of surgical functions appears on display 16. List 120 preferably includes Diathermy, Reflux, Next Mode, Alternate Infusion/Irrigation, Cut/U/S Toggle, and the Next Submode (not shown) functions, which are all the functions currently assigned to switches 56a, 56b, 58a, 58b, 60, and 62 of foot controller 26. The various functions of list 120 can be accessed via a user touching scroll down arrow 110 or scroll up arrow 112, as is conventional. Using list 120, a user can exchange the functions of any two binary switches on foot controller 26. For example, if a user were to touch the Next Mode function in list 120 associated with switch 58a, the Alternate Infusion/Irrigation function would be assigned to left heel switch 60, and the Next Mode function would be assigned to right vertical switch 58a, as shown in FIG. 9. Although not shown in FIG. 8, a user may access a list of functions 120 by touching pull down menu arrow 106 associated with any of switches 56a, 56b, 58b, 60, or 62. In this manner, a surgeon, or his or her nurse, may map any of the functions of microsurgical system 10 or its associated handpieces that are capable of being controlled by foot controller 26 to any of the binary switches 56a, 56b, 58a, 58b, 60, or 62 of controller 26. Such flexibility accommodates the individual preferences of each surgeon. A surgeon may also use such flexibility to minimize the learning curve associated with operating a surgical system 10 that is different from the system he or she typically uses.

Figure 10:
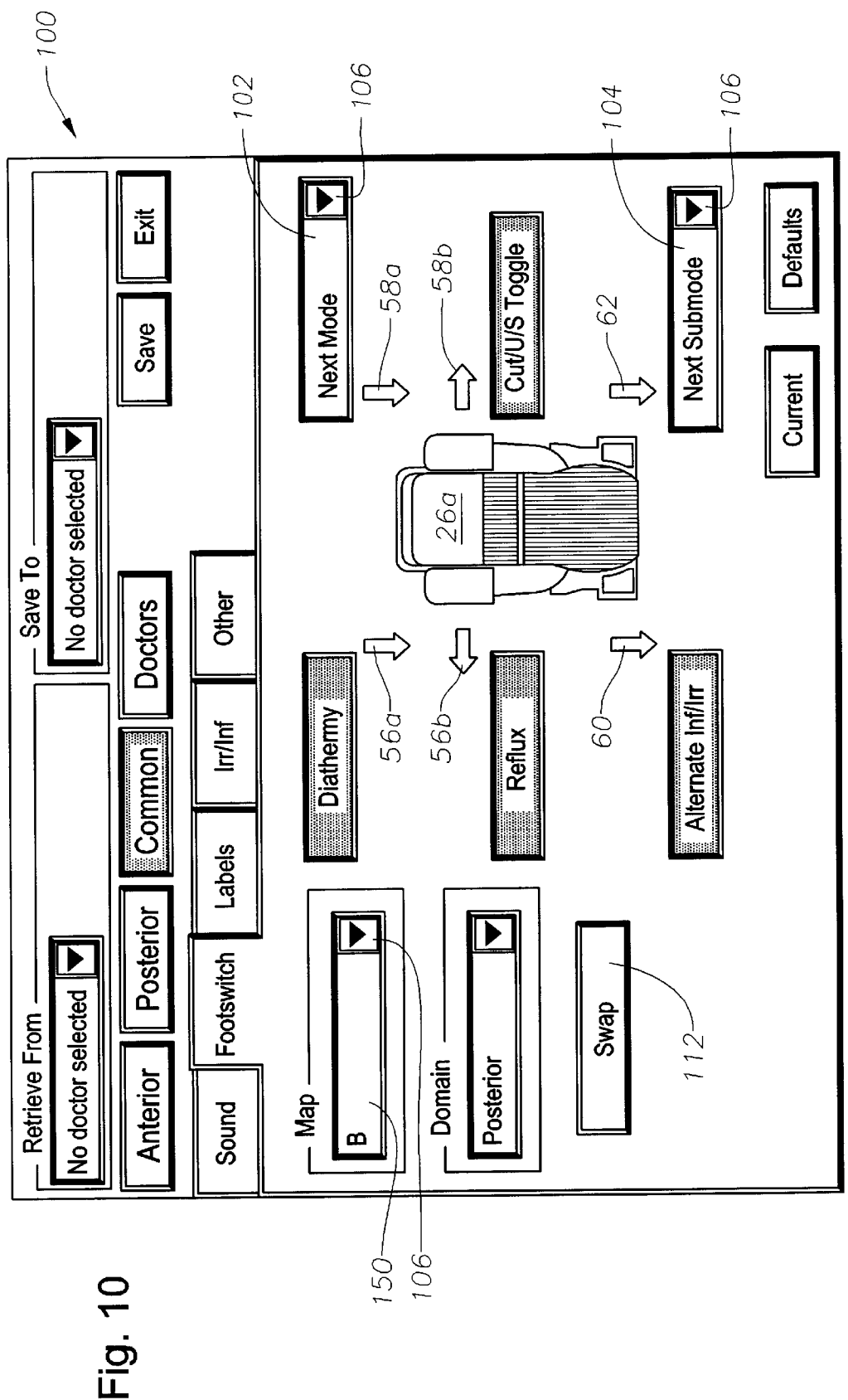

Once the desired mapping of switches 56a, 56b, 58a, 58b, 60, and 62 is accomplished, the user again presses Swap button 112. As shown in FIG. 10, switches 56a, 56b, 58b, and 60 of foot controller 26 are then assigned dedicated functions. Right vertical switch 58a is associated with software generated list 102, which currently has the default function of Next Mode. Right heel switch 62 is associated with software generated list 104, which currently has the default function of Next Submode.

Figure 11:
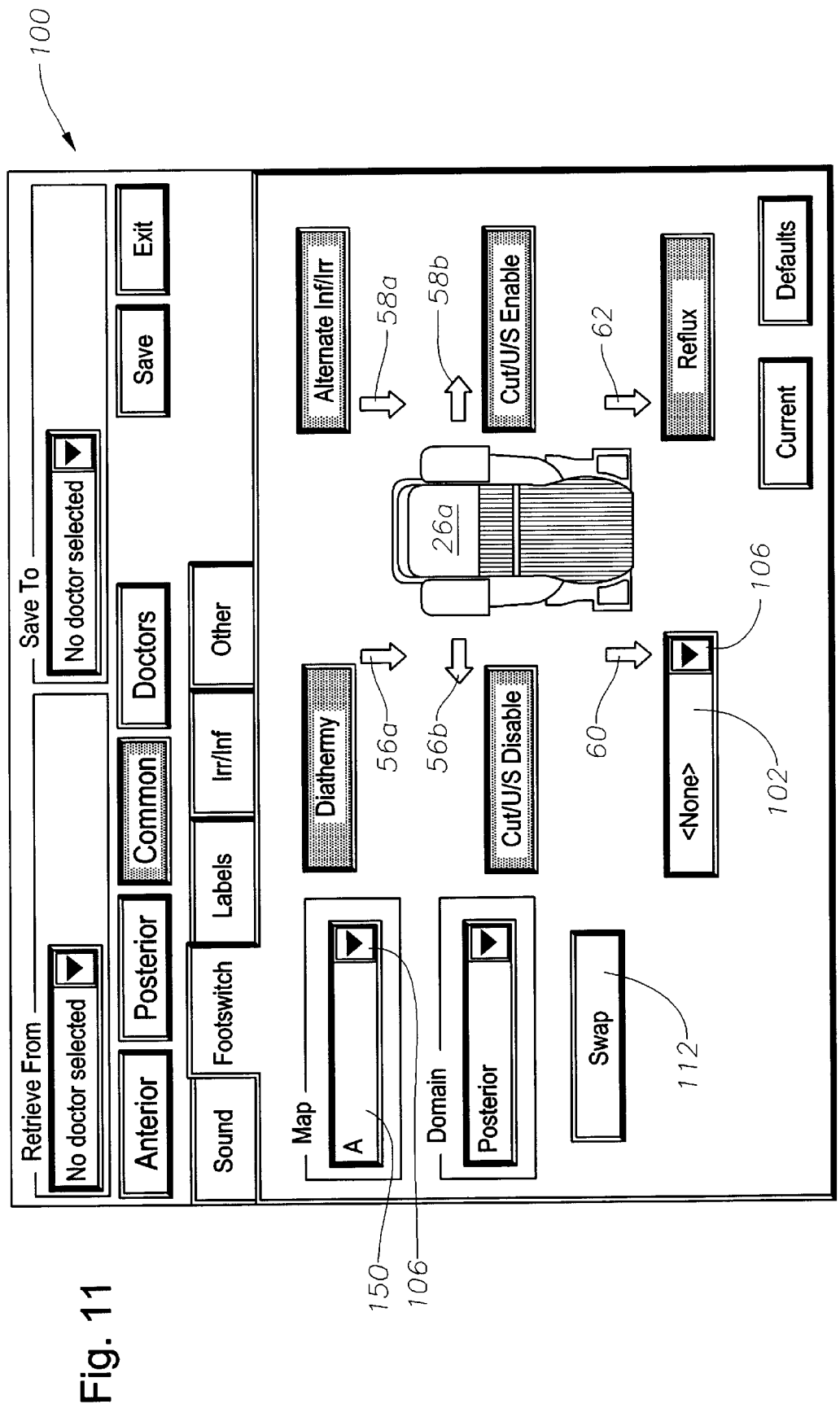
FIG. 11 is a touch screen display of the microsurgical system of FIG. 1 showing a second preferred embodiment of a screen utilized to set up the foot controller of FIG. 2.

Microsurgical system 10 may support multiple maps of the switches of foot controller 26. By way of example, FIG. 11 shows a preferred Map A for switches 56a, 56b, 58a, 58b, 60, and 62. A user may select Map A by touching pull down menu arrow 106 of software generated list 150. In Map A, switch 56a is assigned the Diathermy function, switch 56b is assigned the Cut/Ultrasound Disable function, switch 58a is assigned the Alternate Infusion/Irrigation function, switch 58b is assigned the Cut/Ultrasound Enable function, and right heel switch 62 is assigned the Reflux function. A software generated list 102 is associated with left heel switch 60. Left heel switch 60 is assigned a default function of None, rendering switch 60 inactive. Of course, the function of switch 60 may be altered using software generated list 102 as described hereinabove. In addition, the functions of any two switches of foot controller 26 may be exchanged using Swap button 112 as described hereinabove.

From the above, it may be appreciated that the present invention provides a surgeon with improved flexibility in mapping or programming a foot controller of a microsurgical system, and particularly an ophthalmic microsurgical system. This improved flexibility allows more surgeons to be comfortable using a foot controller to alter the machine settings on the surgical system during surgery, and eliminates the need for a surgeon to converse with a nurse about such machine settings during the surgical procedure.

The present invention is illustrated herein by example, and various modifications may be made by a person of ordinary skill in the art. For example, although the present invention is described hereinabove in connection with a foot controller for an ophthalmic microsurgical system, the present invention is applicable to any microsurgical system, including a system for performing otic, nasal, throat, or other surgeries. As another example, although the present invention is described hereinabove as having up to two of the binary switches of the foot controller associated with a software generated list for assigning the Next Mode, Previous Mode, Next Submode, Previous Submode, Next Memory, or Previous Memory functions, more than two binary switches may be so associated for particular surgical systems. As a further example, other functions may be assigned to the binary switches of the foot controller and/or such software generated lists for particular surgical systems. As a final example, the present invention is applicable to foot controllers that have more or less than six binary switches.

It is believed that the operation and construction of the present invention will be apparent from the foregoing description. While the apparatus and methods shown or described above have been characterized as being preferred, various changes and modifications may be made therein without departing from the spirit and scope of the invention as defined in the following claims.

What is claimed is:

1. A microsurgical system, comprising:

a computer;

a foot controller operatively coupled to said computer, said foot controller having a plurality of switches disposed thereon, each of said switches for controlling a surgical function of said microsurgical system and for actuation by a user's foot;

a touch screen display operatively coupled to said computer, said touch screen display having an ability to:

display a graphical representation of said foot controller including said plurality of switches; and display a list of surgical functions, said list being associated with said graphical representation of one of said plurality of switches;

whereby by touching one of said surgical functions in said list, a user can exchange said surgical functions associated with any two of said plurality of switches on said foot controller.

2. The microsurgical system of claim 1 wherein said list of surgical functions comprises each of said surgical functions currently associated with said plurality of switches on said foot controller.

3. The microsurgical system of claim 1 wherein each of said plurality of switches is a binary switch.

4. The microsurgical system of claim 1 wherein said list of surgical functions is displayed in a pull down menu format.

5. A method of mapping surgical functions of a microsurgical system to a foot controller operatively coupled with said microsurgical system, comprising the steps of:

providing a microsurgical system comprising:

a foot controller having a plurality of switches disposed thereon, each of said switches for controlling a surgical function of said microsurgical system and for actuation by a user's foot; and a touch screen display;

displaying a graphical representation of said foot controller including said plurality of switches on said touch screen display;

displaying a list of surgical functions on said touch screen display, said list being associated with said graphical representation of one of said plurality of switches; and exchanging said surgical functions associated with two of said plurality of switches on said foot controller in response to a user touching one of said surgical functions in said list.

6. The method of claim 5 further comprising repeating said step of displaying a list and said exchanging step to exchange surgical functions associated with more than two of said plurality of switches.

7. The method of claim 5 wherein said step of displaying said list comprises displaying said list in a pull down menu format.

\* \* \* \* \*